US006734009B2

(12) United States Patent
Yu et al.

(10) Patent No.: US 6,734,009 B2
(45) Date of Patent: May 11, 2004

(54) HUMAN KINASES AND POLYNUCLEOTIDES ENCODING THE SAME

(75) Inventors: Xuanchuan (Sean) Yu, Houston, TX (US); Maricar Miranda, Houston, TX (US); Carl Johan Friddle, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 168 days.

(21) Appl. No.: 10/028,946

(22) Filed: Dec. 20, 2001

(65) Prior Publication Data

US 2002/0123622 A1 Sep. 5, 2002

Related U.S. Application Data

(60) Provisional application No. 60/258,335, filed on Dec. 27, 2000.

(51) Int. Cl.$^7$ .......................... C12N 1/20; C12N 15/00; C12N 5/00; C12N 9/20; C07H 21/04
(52) U.S. Cl. .................. 435/252.3; 435/320.1; 435/6; 435/194; 435/325; 536/23.2
(58) Field of Search .................. 435/252.3, 320.1, 435/6, 194, 325; 536/23.2

(56) References Cited

U.S. PATENT DOCUMENTS

| 4,215,051 A | 7/1980 | Schroeder et al. ....... 260/346.7 |
| 4,376,110 A | 3/1983 | David et al. ................ 436/513 |
| 4,594,595 A | 6/1986 | Struckman .................. 343/770 |
| 4,631,211 A | 12/1986 | Houghten ..................... 428/35 |
| 4,689,405 A | 8/1987 | Frank et al. .................. 536/27 |
| 4,713,326 A | 12/1987 | Dattagupta et al. ............. 435/6 |
| 4,873,191 A | 10/1989 | Wagner et al. ............ 435/172.3 |
| 4,946,778 A | 8/1990 | Ladner et al. ............. 435/69.6 |
| 5,252,743 A | 10/1993 | Barrett et al. ............ 548/303.7 |
| 5,272,057 A | 12/1993 | Smulson et al. ................ 435/6 |
| 5,424,186 A | 6/1995 | Fodor et al. .................... 435/6 |
| 5,445,934 A | 8/1995 | Fodor et al. .................... 435/6 |
| 5,459,127 A | 10/1995 | Felgner et al. .................. 514/7 |
| 5,556,752 A | 9/1996 | Lockhart et al. ................ 435/6 |
| 5,700,637 A | 12/1997 | Southern ....................... 435/6 |
| 5,723,323 A | 3/1998 | Kauffman et al. ........ 435/172.3 |
| 5,744,305 A | 4/1998 | Fodor et al. .................... 435/6 |
| 5,830,721 A | 11/1998 | Stemmer et al. ......... 435/172.1 |
| 5,837,458 A | 11/1998 | Minshull et al. ................ 435/6 |
| 5,869,336 A | 2/1999 | Meyer et al. ................ 435/348 |
| 5,877,397 A | 3/1999 | Lonberg et al. ................. 800/2 |
| 5,948,767 A | 9/1999 | Scheule et al. ................ 514/44 |
| 6,075,181 A | 6/2000 | Kucherlapati et al. ......... 800/25 |
| 6,110,490 A | 8/2000 | Thierry ....................... 424/450 |
| 6,117,679 A | 9/2000 | Stemmer ..................... 435/440 |
| 6,150,584 A | 11/2000 | Kucherlapati et al. ........ 800/18 |

FOREIGN PATENT DOCUMENTS

| WO | WO 99/25843 A2 | 5/1999 |
| WO | WO 01/38503 A2 | 5/2001 |

OTHER PUBLICATIONS

Database EMBL_HTG 'Online' "*Homo sapiens* chromosome 12 clone RP11–184J5," Mar. 23, 2000, database accession No. AC026363, XP002220103, Mar. 23, 2000.

Nagase et al., "Prediction of the coding sequence of unidentified human genes. XIII. The complete sequence of 100 new cDNA clones from brain which code for large proteins in vitro," DNA Research, Universal Academy Press, JP, vol. 6, 1999, pp. 63–70, XP000952912, ISSN: 1340–2838.

Di Cunto, et al., "Citron Rho–interacting kinase, a novel tissue–specific Ser/Thr kinase encompassing the Rho–Rac–binding protein citron," Journal of Biological Chemistry, vol. 273, No. 45, Nov. 6, 1998, pp. 29706–29711, XP002170360, ISSN: 0021–9258.

International Search Report, International Application No. PCT/US01/50497, Dec. 20, 2001.

Logan et al, 1984, "Adenovirus tripartite leader sequence enhances translation of mRNAs late after infection", Proc. Natl. Acad. Sci. USA 81:3655–3659.

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

(List continued on next page.)

*Primary Examiner*—Maryam Monshipouri

(57) ABSTRACT

Novel human polynucleotide and polypeptide sequences are disclosed that can be used in therapeutic, diagnostic, and pharmacogenomic applications.

5 Claims, No Drawings

OTHER PUBLICATIONS

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Cote et al., 1983, "Generation of human monoclonal antibodies reactive with cellular antigens," Proc. Natl. Acad. Sci. USA 80:2026–2030.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Gordon, 1989, "Transgenic Animals", International Review of Cytology, 115:171–229.

Greenspan et al, 1993 "Idiotypes: structure and immunogenicity", FASEB Journal 7:437–444.

Gu et al, 1994, "Deletion of a DNA Polymerase β Gene Segment in T Cells Using Cell Type–Specific Gene Targeting", Science 265:103–106.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'–O–methyl)ribonucleotides", Nucleic Acids Research 15(15):6131–6149.

Inouye & Inouye, 1985, "Up–promoter mutations in the Ipp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS USA 88:8972–8976.

Kohler & Milstein, 1975, "Continuous cultures of fused cells secreting antibody of predefined specificity", Nature 256:495–497.

Lakso et al, 1992, "Targeted oncogene activation by site–specific recombination in transgenic mice", Proc. Natl. Acad. Sci. USA 89:6232–6236.

Lavitrano'et al, 1989, "Sperm Cells as Vectors for Introducing Foreign DNA into Eggs: Genetic Transformation of Mice", Cell 57:717–723.

Lo, 1983, "Transformation by Iontophoretic Microinjection of DNA: Multiple Integrations without Tandem Insertions", Mol. & Cell. Biology 3(10):1803–1814.

SEQUENCE LISTING

<160> NUMBER OF SEQ ID NOS: 4

<210> SEQ ID NO 1
<211> LENGTH: 6165
<212> TYPE: DNA
<213> ORGANISM: homo sapiens

<400> SEQUENCE: 1

| | | | | | |
|---|---|---|---|---|---|
| atgttgaagt | tcaaatatgg | agcgcggaat | cctttggatg | ctggtgctgc | tgaacccatt | 60 |
| gccagccggg | cctccaggct | gaatctgttc | ttccagggga | aaccaccctt | tatgactcaa | 120 |
| cagcagatgt | ctcctctttc | ccgagaaggg | atattagatg | ccctctttgt | tctcttgaa | 180 |
| gaatgcagtc | agcctgctct | gatgaagatt | aagcacgtga | gcaactttgt | ccggaagtat | 240 |
| tccgacacca | tagctgagtt | acaggagctc | cagccttcgg | caaaggactt | cgaagtcaga | 300 |
| agtcttgtag | gttgtggtca | ctttgctgaa | gtgcaggtgg | taagagagaa | agcaaccggg | 360 |
| gacatctatg | ctatgaaagt | gatgaagaag | aaggctttat | tggcccagga | gcaggtttca | 420 |
| tttttgagg | aagagcggaa | catattatct | cgaagcacaa | gcccgtggat | ccccaatta | 480 |
| cagtatgcct | tcaggacaa | aaatcacctt | tatctggtca | tggaatatca | gcctggaggg | 540 |
| gacttgctgt | cacttttgaa | tagatatgag | gaccagttag | atgaaaacct | gatacagttt | 600 |
| tacctagctg | agctgatttt | ggctgttcac | agcgttcatc | tgatgggata | cgtgcatcga | 660 |
| gacatcaagc | ctgagaacat | tctcgttgac | cgcacaggac | acatcaagct | ggtggatttt | 720 |
| ggatctgccg | cgaaaatgaa | ttcaaacaag | atggtgaatg | ccaaactccc | gattgggacc | 780 |
| ccagattaca | tggctcctga | agtgctgact | gtgatgaacg | gggatggaaa | aggcacctac | 840 |
| ggcctggact | gtgactggtg | gtcagtgggc | gtgattgcct | atgagatgat | ttatgggaga | 900 |
| tccccctcg | cagagggaac | ctctgccaga | accttcaata | acattatgaa | tttccagcgg | 960 |
| ttttgaaat | ttccagatga | ccccaaagtg | agcagtgact | ttcttgatct | gattcaaagc | 1020 |
| ttgttgtgcg | gccagaaaga | gagactgaag | tttgaaggtc | tttgctgcca | tcctttcttc | 1080 |
| tctaaaattg | actggaacaa | cattcgtaac | tctcctcccc | ccttcgttcc | caccctcaag | 1140 |
| tctgacgatg | acacctccaa | ttttgatgaa | ccagagaaga | attcgtgggt | ttcatcctct | 1200 |
| ccgtgccagc | tgagcccctc | aggcttctcg | ggtgaagaac | tgccgtttgt | ggggttttcg | 1260 |
| tacagcaagg | cactggggat | tcttggtaga | tctgagtctg | ttgtgtcggg | tctggactcc | 1320 |
| cctgccaaga | ctagctccat | ggaaaagaaa | cttctcatca | aaagcaaaga | gctacaagac | 1380 |
| tctcaggaca | agtgtcacaa | gatggagcag | gaaatgaccc | ggttacatcg | gagagtgtca | 1440 |
| gaggtggagg | ctgtgcttag | tcagaaggag | gtggagctga | aggcctctga | gactcagaga | 1500 |
| tccctcctgg | agcaggacct | tgctacctac | atcacagaat | gcagtagctt | aaagcgaagt | 1560 |
| ttggagcaag | cacggatgga | ggtgtcccag | gaggatgaca | aagcactgca | gcttctccat | 1620 |

-continued

```
gatatcagag agcagagccg gaagctccaa gaaatcaaag agcaggagta ccaggctcaa   1680
gtggaagaaa tgaggttgat gatgaatcag ttggaagagg atcttgtctc agcaagaaga   1740
cggagtgatc tctacgaatc tgagctgaga gagtctcggc ttgctgctga agaattcaag   1800
cggaaagcga cagaatgtca gcataaactg ttgaaggcta aggatcaagg gaagcctgaa   1860
gtgggagaat atgcgaaact ggagaagatc aatgctgagc agcagctcaa aattcaggag   1920
ctccaagaga aactggagaa ggctgtaaaa gccagcacgg aggccaccga gctgctgcag   1980
aatatccgcc aggcaaagga gcgagccgag agggagctgg agaagctgca gaaccgagag   2040
gattcttctg aaggcatcag aaagaagctg gtggaagctg aggaacgccg ccattctctg   2100
gagaacaagg taaagagact agagaccatg gagcgtagag aaaacagact gaaggatgac   2160
atccagacaa atcccaaca gatccagcag atggctgata aaattctgga gctcgaagag   2220
aaacatcggg aggcccaagt ctcagcccag cacctagaag tgcacctgaa acagaaagag   2280
cagcactatg aggaaaagat taaagtgttg acaatcaga taaagaaaga cctggctgac   2340
aaggagacac tggagaacat gatgcagaga cacgaggagg aggcccatga aagggcaaa   2400 attctcagcg aacagaaggc gatgatcaat gctatggatt ccaagatcag atccctggaa   2460
cagaggattg tggaactgtc tgaagccaat aaacttgcag caaatagcag tcttttacc   2520 caaaggaaca tgaaggccca agaagagatg atttctgaac tcaggcaaca gaaattttac   2580
ctggagacac aggctgggaa gttggaggcc cagaaccgaa aactggagga gcagctggag   2640
aagatcagcc accaagacca cagtgacaag aatcggctgc tggaactgga gacaagattg   2700
cgggaggtca gtctagagca cgaggagcag aaactggagc tcaagcgcca gctcacagag   2760
ctacagctct ccctgcagga gcgcgagtca cagttgacag ccctgcaggc tgcacgggcg   2820
gccctggaga gccagcttcg ccaggcgaag acagagctgg aagagaccac agcagaagct   2880
gaagaggaga tccaggcact cacggcacat agagatgaaa tccagcgcaa atttgatgct   2940
cttcgtaaca gctgtactgt aatcacagac ctggaggagc agctaaacca gctgaccgag   3000
gacaacgctg aactcaacaa ccaaaacttc tacttgtcca acaactcga tgaggcttct   3060 ggcgccaacg acgagattgt acaactgcga agtgaagtgg accatctccg ccgggagatc   3120
acggaacaga gatgcagct taccagccag aagcaaacga tggaggctct gaagaccacg   3180
tgcaccatgc tggaggaaca ggtcatggat ttggaggccc taaacgatga gctgctagaa   3240
aaagagcggc agtgggaggc ctggaggagc gtcctgggtg atgagaaatc ccagtttgag   3300
tgtcgggttc gagagctgca gaggatgctg acaccgaga acagagcag gcgagagcc   3360 gatcagcgga tcaccgagtc tcgccaggtg gtggagctgg cagtgaagga gcacaaggct   3420
gagattctcg ctctgcagca ggctctcaaa gagcagaagc tgaaggccga gagcctctct   3480
gacaagctca atgacctgga agaagcat gctatgcttg aaatgaatgc ccgaagctta   3540
cagcagaagc tggagactga acgagagctc aaacagaggc ttctggaaga gcaagccaaa   3600
ttacagcagc agatggacct gcagaaaaat cacattttcc gtctgactca aggactgcaa   3660
gaagctctag atcgggctga tctactgaag acagaaagaa gtgacttgga gtatcagctg   3720
gaaaacattc aggttctcta ttctcatgaa aaggtgaaaa tggaaggcac tatttctcaa   3780
caaaccaaac tcattgattt tctgcaagcc aaaatggacc aacctgctaa aagaaaaag   3840 gttcctctgc agtacaatga gctgaagctg gccctggaga aggagaaagc tcgctgtgca   3900
gagctagagg aagcccttca gaagacccgc atcgagctcc ggtccgcccg ggaggaagct   3960
gcccaccgca agcaacgga ccacccacac ccatccacgc cagccaccgc gaggcagcag   4020
```

-continued

```
atcgccatgt ccgccatcgt gcggtcgcca gagcaccagc ccagtgccat gagcctgctg    4080
gccccgccat ccagccgcag aaaggagtct tcaactccag aggaatttag tcggcgtctt    4140
aaggaacgca tgcaccacaa tattcctcac cgattcaacg taggactgaa catgcgagcc    4200
acaaagtgtg ctgtgtgtct ggataccgtg cactttggac gccaggcatc caaatgtctc    4260
gaatgtcagg tgatgtgtca ccccaagtgc tccacgtgct tgccagccac ctgcggcttg    4320
cctgctgaat atgccacaca cttcaccgag gccttctgcc gtgacaaaat gaactcccca    4380
ggtctccaga ccaaggagcc cagcagcagc ttgcacctgg aagggtggat gaaggtgccc    4440
aggaataaca aacgaggaca gcaaggctgg gacaggaagt acattgtcct ggagggatca    4500
aaagtcctca tttatgacaa tgaagccaga gaagctggac agaggccggt ggaagaattt    4560
gagctgtgcc ttcccgacgg ggatgtatct attcatggtg ccgttggtgc ttccgaactc    4620
gcaaatacag ccaaagcaga tgtcccatac atactgaaga tggaatctca cccgcacacc    4680
acctgctggc ccgggagaac cctctacttg ctagctccca gcttccctga caaacagcgc    4740
tgggtcaccg ccttagaatc agttgtcgca ggtgggagag tttctaggga aaaagcagaa    4800
gctgatgcta aactgcttgg aaactccctg ctgaaactgg aaggtgatga ccgtctagac    4860
atgaactgca cgctgcccct cagtgaccag gtggtgttgg tgggcaccga ggaagggctc    4920
tacgccctga atgtcttgaa aaactcccta acccatgtcc caggaattgg agcagtcttc    4980
caaatttata ttatcaagga cctggagaag ctactcatga tagcaggaga gagcgggca    5040 ctgtgtcttg tggacgtgaa gaaagtgaaa cagtccctgg cccagtccca cctgcctgcc    5100
cagcccgaca tctcacccaa cattttgaa gctgtcaagg ctgccacttg tttggggca     5160 ggcaagattg agaacgggct ctgcatctgt gcagccatgc cagcaaagt cgtcattctc     5220 cgctacaacg aaaaccctcag caaatactgc atccggaaag agatagagac ctcagagccc    5280
tgcagctgta tccacttcac caattacagt atcctcattg gaaccaataa attctacgaa    5340
atcgacatga agcagtacac gctcgaggaa ttcctggata agaatgacca ttccttggca    5400
cctgctgtgt ttgccgcctc ttccaacagc ttccctgtct caatcgtgca ggtgaacagc    5460
gcagggcagc gagaggagta cttgctgtgt ttccacgaat ttggagtgtt cgtggattct    5520
tacggaagac gtagccgcac agacgatctc aagtggagtc gcttacctt ggcctttgcc     5580 tacagagaac cctatctgtt tgtgacccac ttcaactcac tcgaagtaat tgagatccag    5640
gcacgctcct cagcagggac ccctgcccga gcgtacctgg acatcccgaa cccgcgctac    5700
ctgggccctg ccatttcctc aggagcgatt tacttggcgt cctcatacca ggataaatta    5760
agggtcattt gctgcaaggg aaacctcgtg aaggagtccg gcactgaaca ccaccggggc    5820
ccgtccacct cccgcagcag ccccaacaag cgaggcccac ccacgtacaa cgagcacatc    5880
accaagcgcg tggcctccag cccagcgccg cccgaaggcc ccagccaccc gcgagagcca    5940
agcacacccc accgctaccg cgaggggcgg accgagctgc gcaggacaa gtctcctggc    6000 cgcccctga gcgagagaa gtcccccggc cggatactca gcacgcggag agagcggtcc     6060
cccgcgaggc tgtttgaaga cagcagcagg ggccggctgc ctgcgggagc cgtgaggacc    6120
ccgctgtccc aggtgaacaa ggtctgggac cagtcttcag tataa                    6165
```

<210> SEQ ID NO 2
<211> LENGTH: 2054
<212> TYPE: PRT
<213> ORGANISM: homo sapiens -continued

<400> SEQUENCE: 2

```
Met Leu Lys Phe Lys Tyr Gly Ala Arg Asn Pro Leu Asp Ala Gly Ala
 1               5                  10                  15
Ala Glu Pro Ile Ala Ser Arg Ala Ser Arg Leu Asn Leu Phe Phe Gln
            20                  25                  30
Gly Lys Pro Pro Phe Met Thr Gln Gln Met Ser Pro Leu Ser Arg
        35                  40                  45
Glu Gly Ile Leu Asp Ala Leu Phe Val Leu Phe Glu Glu Cys Ser Gln
 50                  55                  60
Pro Ala Leu Met Lys Ile Lys His Val Ser Asn Phe Val Arg Lys Tyr
 65                  70                  75                  80
Ser Asp Thr Ile Ala Glu Leu Gln Glu Leu Gln Pro Ser Ala Lys Asp
                85                  90                  95
Phe Glu Val Arg Ser Leu Val Gly Cys Gly His Phe Ala Glu Val Gln
            100                 105                 110
Val Val Arg Glu Lys Ala Thr Gly Asp Ile Tyr Ala Met Lys Val Met
        115                 120                 125
Lys Lys Lys Ala Leu Leu Ala Gln Glu Gln Val Ser Phe Phe Glu Glu
130                 135                 140
Glu Arg Asn Ile Leu Ser Arg Ser Thr Ser Pro Trp Ile Pro Gln Leu
145                 150                 155                 160
Gln Tyr Ala Phe Gln Asp Lys Asn His Leu Tyr Leu Val Met Glu Tyr
                165                 170                 175
Gln Pro Gly Gly Asp Leu Leu Ser Leu Leu Asn Arg Tyr Glu Asp Gln
            180                 185                 190
Leu Asp Glu Asn Leu Ile Gln Phe Tyr Leu Ala Glu Leu Ile Leu Ala
        195                 200                 205
Val His Ser Val His Leu Met Gly Tyr Val His Arg Asp Ile Lys Pro
210                 215                 220
Glu Asn Ile Leu Val Asp Arg Thr Gly His Ile Lys Leu Val Asp Phe
225                 230                 235                 240
Gly Ser Ala Ala Lys Met Asn Ser Asn Lys Met Val Asn Ala Lys Leu
                245                 250                 255
Pro Ile Gly Thr Pro Asp Tyr Met Ala Pro Glu Val Leu Thr Val Met
            260                 265                 270
Asn Gly Asp Gly Lys Gly Thr Tyr Gly Leu Asp Cys Asp Trp Trp Ser
        275                 280                 285
Val Gly Val Ile Ala Tyr Glu Met Ile Tyr Gly Arg Ser Pro Phe Ala
290                 295                 300
Glu Gly Thr Ser Ala Arg Thr Phe Asn Asn Ile Met Asn Phe Gln Arg
305                 310                 315                 320
Phe Leu Lys Phe Pro Asp Asp Pro Lys Val Ser Ser Asp Phe Leu Asp
                325                 330                 335
Leu Ile Gln Ser Leu Leu Cys Gly Gln Lys Glu Arg Leu Lys Phe Glu
            340                 345                 350
Gly Leu Cys Cys His Pro Phe Phe Ser Lys Ile Asp Trp Asn Asn Ile
        355                 360                 365
Arg Asn Ser Pro Pro Pro Phe Val Pro Thr Leu Lys Ser Asp Asp Asp
370                 375                 380
Thr Ser Asn Phe Asp Glu Pro Glu Lys Asn Ser Trp Val Ser Ser Ser
385                 390                 395                 400
Pro Cys Gln Leu Ser Pro Ser Gly Phe Ser Gly Glu Glu Leu Pro Phe
                405                 410                 415
```

```
Val Gly Phe Ser Tyr Ser Lys Ala Leu Gly Ile Leu Gly Arg Ser Glu
            420                 425                 430

Ser Val Val Ser Gly Leu Asp Ser Pro Ala Lys Thr Ser Ser Met Glu
            435                 440                 445

Lys Lys Leu Leu Ile Lys Ser Lys Glu Leu Gln Asp Ser Gln Asp Lys
            450                 455                 460

Cys His Lys Met Glu Gln Glu Met Thr Arg Leu His Arg Arg Val Ser
465                 470                 475                 480

Glu Val Glu Ala Val Leu Ser Gln Lys Glu Val Glu Leu Lys Ala Ser
            485                 490                 495

Glu Thr Gln Arg Ser Leu Leu Glu Gln Asp Leu Ala Thr Tyr Ile Thr
            500                 505                 510

Glu Cys Ser Ser Leu Lys Arg Ser Leu Glu Gln Ala Arg Met Glu Val
            515                 520                 525

Ser Gln Glu Asp Asp Lys Ala Leu Gln Leu Leu His Asp Ile Arg Glu
            530                 535                 540

Gln Ser Arg Lys Leu Gln Glu Ile Lys Glu Gln Glu Tyr Gln Ala Gln
545                 550                 555                 560

Val Glu Glu Met Arg Leu Met Met Asn Gln Leu Glu Glu Asp Leu Val
            565                 570                 575

Ser Ala Arg Arg Arg Ser Asp Leu Tyr Glu Ser Glu Leu Arg Glu Ser
            580                 585                 590

Arg Leu Ala Ala Glu Glu Phe Lys Arg Lys Ala Thr Glu Cys Gln His
            595                 600                 605

Lys Leu Leu Lys Ala Lys Asp Gln Gly Lys Pro Glu Val Gly Glu Tyr
            610                 615                 620

Ala Lys Leu Glu Lys Ile Asn Ala Glu Gln Gln Leu Lys Ile Gln Glu
625                 630                 635                 640

Leu Gln Glu Lys Leu Glu Lys Ala Val Lys Ala Ser Thr Glu Ala Thr
            645                 650                 655

Glu Leu Leu Gln Asn Ile Arg Gln Ala Lys Glu Arg Ala Glu Arg Glu
            660                 665                 670

Leu Glu Lys Leu Gln Asn Arg Glu Asp Ser Ser Glu Gly Ile Arg Lys
            675                 680                 685

Lys Leu Val Glu Ala Glu Arg Arg His Ser Leu Glu Asn Lys Val
            690                 695                 700

Lys Arg Leu Glu Thr Met Glu Arg Glu Asn Arg Leu Lys Asp Asp
705                 710                 715                 720

Ile Gln Thr Lys Ser Gln Gln Ile Gln Gln Met Ala Asp Lys Ile Leu
            725                 730                 735

Glu Leu Glu Glu Lys His Arg Glu Ala Gln Val Ser Ala Gln His Leu
            740                 745                 750

Glu Val His Leu Lys Gln Lys Glu Gln His Tyr Glu Glu Lys Ile Lys
            755                 760                 765

Val Leu Asp Asn Gln Ile Lys Lys Asp Leu Ala Asp Lys Glu Thr Leu
            770                 775                 780

Glu Asn Met Met Gln Arg His Glu Glu Glu Ala His Glu Lys Gly Lys
785                 790                 795                 800

Ile Leu Ser Glu Gln Lys Ala Met Ile Asn Ala Met Asp Ser Lys Ile
            805                 810                 815

Arg Ser Leu Glu Gln Arg Ile Val Glu Leu Ser Glu Ala Asn Lys Leu
            820                 825                 830
```

```
Ala Ala Asn Ser Ser Leu Phe Thr Gln Arg Asn Met Lys Ala Gln Glu
        835                 840                 845

Glu Met Ile Ser Glu Leu Arg Gln Gln Lys Phe Tyr Leu Glu Thr Gln
    850                 855                 860

Ala Gly Lys Leu Glu Ala Gln Asn Arg Lys Leu Glu Glu Gln Leu Glu
865                 870                 875                 880

Lys Ile Ser His Gln Asp His Ser Asp Lys Asn Arg Leu Leu Glu Leu
            885                 890                 895

Glu Thr Arg Leu Arg Glu Val Ser Leu Glu His Glu Glu Gln Lys Leu
        900                 905                 910

Glu Leu Lys Arg Gln Leu Thr Glu Leu Gln Leu Ser Leu Gln Glu Arg
    915                 920                 925

Glu Ser Gln Leu Thr Ala Leu Gln Ala Ala Arg Ala Ala Leu Glu Ser
    930                 935                 940

Gln Leu Arg Gln Ala Lys Thr Glu Leu Glu Glu Thr Thr Ala Glu Ala
945                 950                 955                 960

Glu Glu Glu Ile Gln Ala Leu Thr Ala His Arg Asp Glu Ile Gln Arg
            965                 970                 975

Lys Phe Asp Ala Leu Arg Asn Ser Cys Thr Val Ile Thr Asp Leu Glu
        980                 985                 990

Glu Gln Leu Asn Gln Leu Thr Glu Asp Asn Ala Glu Leu Asn Asn Gln
    995                 1000                1005

Asn Phe Tyr Leu Ser Lys Gln Leu Asp Glu Ala Ser Gly Ala Asn Asp
    1010                1015                1020

Glu Ile Val Gln Leu Arg Ser Glu Val Asp His Leu Arg Arg Glu Ile
1025                1030                1035                1040

Thr Glu Arg Glu Met Gln Leu Thr Ser Gln Lys Gln Thr Met Glu Ala
            1045                1050                1055

Leu Lys Thr Thr Cys Thr Met Leu Glu Glu Gln Val Met Asp Leu Glu
        1060                1065                1070

Ala Leu Asn Asp Glu Leu Leu Glu Lys Glu Arg Gln Trp Glu Ala Trp
    1075                1080                1085

Arg Ser Val Leu Gly Asp Glu Lys Ser Gln Phe Glu Cys Arg Val Arg
    1090                1095                1100

Glu Leu Gln Arg Met Leu Asp Thr Glu Lys Gln Ser Arg Ala Arg Ala
1105                1110                1115                1120

Asp Gln Arg Ile Thr Glu Ser Arg Gln Val Val Glu Leu Ala Val Lys
            1125                1130                1135

Glu His Lys Ala Glu Ile Leu Ala Leu Gln Gln Ala Leu Lys Glu Gln
        1140                1145                1150

Lys Leu Lys Ala Glu Ser Leu Ser Asp Lys Leu Asn Asp Leu Glu Lys
    1155                1160                1165

Lys His Ala Met Leu Glu Met Asn Ala Arg Ser Leu Gln Gln Lys Leu
    1170                1175                1180

Glu Thr Glu Arg Glu Leu Lys Gln Arg Leu Leu Glu Glu Gln Ala Lys
1185                1190                1195                1200

Leu Gln Gln Gln Met Asp Leu Gln Lys Asn His Ile Phe Arg Leu Thr
            1205                1210                1215

Gln Gly Leu Gln Glu Ala Leu Asp Arg Ala Asp Leu Leu Lys Thr Glu
        1220                1225                1230

Arg Ser Asp Leu Glu Tyr Gln Leu Glu Asn Ile Gln Val Leu Tyr Ser
    1235                1240                1245

His Glu Lys Val Lys Met Glu Gly Thr Ile Ser Gln Gln Thr Lys Leu
```

-continued

```
                1250                1255                1260
Ile Asp Phe Leu Gln Ala Lys Met Asp Gln Pro Ala Lys Lys Lys
1265                1270                1275                1280
Val Pro Leu Gln Tyr Asn Glu Leu Lys Leu Ala Leu Glu Lys Glu Lys
                    1285                1290                1295
Ala Arg Cys Ala Glu Leu Glu Glu Ala Leu Gln Lys Thr Arg Ile Glu
                1300                1305                1310
Leu Arg Ser Ala Arg Glu Glu Ala Ala His Arg Lys Ala Thr Asp His
                1315                1320                1325
Pro His Pro Ser Thr Pro Ala Thr Ala Arg Gln Gln Ile Ala Met Ser
            1330                1335                1340
Ala Ile Val Arg Ser Pro Glu His Gln Pro Ser Ala Met Ser Leu Leu
1345                1350                1355                1360
Ala Pro Pro Ser Ser Arg Arg Lys Glu Ser Ser Thr Pro Glu Glu Phe
                    1365                1370                1375
Ser Arg Arg Leu Lys Glu Arg Met His His Asn Ile Pro His Arg Phe
                1380                1385                1390
Asn Val Gly Leu Asn Met Arg Ala Thr Lys Cys Ala Val Cys Leu Asp
        1395                1400                1405
Thr Val His Phe Gly Arg Gln Ala Ser Lys Cys Leu Glu Cys Gln Val
            1410                1415                1420
Met Cys His Pro Lys Cys Ser Thr Cys Leu Pro Ala Thr Cys Gly Leu
1425                1430                1435                1440
Pro Ala Glu Tyr Ala Thr His Phe Thr Glu Ala Phe Cys Arg Asp Lys
                    1445                1450                1455
Met Asn Ser Pro Gly Leu Gln Thr Lys Glu Pro Ser Ser Ser Leu His
                1460                1465                1470
Leu Glu Gly Trp Met Lys Val Pro Arg Asn Asn Lys Arg Gly Gln Gln
            1475                1480                1485
Gly Trp Asp Arg Lys Tyr Ile Val Leu Glu Gly Ser Lys Val Leu Ile
            1490                1495                1500
Tyr Asp Asn Glu Ala Arg Glu Ala Gly Gln Arg Pro Val Glu Glu Phe
1505                1510                1515                1520
Glu Leu Cys Leu Pro Asp Gly Asp Val Ser Ile His Gly Ala Val Gly
                    1525                1530                1535
Ala Ser Glu Leu Ala Asn Thr Ala Lys Ala Asp Val Pro Tyr Ile Leu
                1540                1545                1550
Lys Met Glu Ser His Pro His Thr Thr Cys Trp Pro Gly Arg Thr Leu
            1555                1560                1565
Tyr Leu Leu Ala Pro Ser Phe Pro Asp Lys Gln Arg Trp Val Thr Ala
        1570                1575                1580
Leu Glu Ser Val Val Ala Gly Gly Arg Val Ser Arg Glu Lys Ala Glu
1585                1590                1595                1600
Ala Asp Ala Lys Leu Leu Gly Asn Ser Leu Leu Lys Leu Glu Gly Asp
                    1605                1610                1615
Asp Arg Leu Asp Met Asn Cys Thr Leu Pro Phe Ser Asp Gln Val Val
                1620                1625                1630
Leu Val Gly Thr Glu Glu Gly Leu Tyr Ala Leu Asn Val Leu Lys Asn
            1635                1640                1645
Ser Leu Thr His Val Pro Gly Ile Gly Ala Val Phe Gln Ile Tyr Ile
        1650                1655                1660
Ile Lys Asp Leu Glu Lys Leu Leu Met Ile Ala Gly Glu Glu Arg Ala
1665                1670                1675                1680
```

```
Leu Cys Leu Val Asp Val Lys Lys Val Lys Gln Ser Leu Ala Gln Ser
                1685                1690                1695

His Leu Pro Ala Gln Pro Asp Ile Ser Pro Asn Ile Phe Glu Ala Val
            1700                1705                1710

Lys Gly Cys His Leu Phe Gly Ala Gly Lys Ile Glu Asn Gly Leu Cys
            1715                1720                1725

Ile Cys Ala Ala Met Pro Ser Lys Val Val Ile Leu Arg Tyr Asn Glu
        1730                1735                1740

Asn Leu Ser Lys Tyr Cys Ile Arg Lys Glu Ile Glu Thr Ser Glu Pro
1745                1750                1755                1760

Cys Ser Cys Ile His Phe Thr Asn Tyr Ser Leu Ile Gly Thr Asn
                1765                1770                1775

Lys Phe Tyr Glu Ile Asp Met Lys Gln Tyr Thr Leu Glu Glu Phe Leu
            1780                1785                1790

Asp Lys Asn Asp His Ser Leu Ala Pro Ala Val Phe Ala Ala Ser Ser
            1795                1800                1805

Asn Ser Phe Pro Val Ser Ile Val Gln Val Asn Ser Ala Gly Gln Arg
        1810                1815                1820

Glu Glu Tyr Leu Leu Cys Phe His Glu Phe Gly Val Phe Val Asp Ser
1825                1830                1835                1840

Tyr Gly Arg Arg Ser Arg Thr Asp Asp Leu Lys Trp Ser Arg Leu Pro
                1845                1850                1855

Leu Ala Phe Ala Tyr Arg Glu Pro Tyr Leu Phe Val Thr His Phe Asn
            1860                1865                1870

Ser Leu Glu Val Ile Glu Ile Gln Ala Arg Ser Ser Ala Gly Thr Pro
        1875                1880                1885

Ala Arg Ala Tyr Leu Asp Ile Pro Asn Pro Arg Tyr Leu Gly Pro Ala
        1890                1895                1900

Ile Ser Ser Gly Ala Ile Tyr Leu Ala Ser Ser Tyr Gln Asp Lys Leu
1905                1910                1915                1920

Arg Val Ile Cys Cys Lys Gly Asn Leu Val Lys Glu Ser Gly Thr Glu
                1925                1930                1935

His His Arg Gly Pro Ser Thr Ser Arg Ser Ser Pro Asn Lys Arg Gly
            1940                1945                1950

Pro Pro Thr Tyr Asn Glu His Ile Thr Lys Arg Val Ala Ser Ser Pro
            1955                1960                1965

Ala Pro Pro Glu Gly Pro Ser His Pro Arg Glu Pro Ser Thr Pro His
        1970                1975                1980

Arg Tyr Arg Glu Gly Arg Thr Glu Leu Arg Arg Asp Lys Ser Pro Gly
1985                1990                1995                2000

Arg Pro Leu Glu Arg Glu Lys Ser Pro Gly Arg Ile Leu Ser Thr Arg
                2005                2010                2015

Arg Glu Arg Ser Pro Ala Arg Leu Phe Glu Asp Ser Ser Arg Gly Arg
            2020                2025                2030

Leu Pro Ala Gly Ala Val Arg Thr Pro Leu Ser Gln Val Asn Lys Val
            2035                2040                2045

Trp Asp Gln Ser Ser Val
    2050

<210> SEQ ID NO 3
<211> LENGTH: 5877
<212> TYPE: DNA
<213> ORGANISM: homo sapiens
```

-continued

```
<400> SEQUENCE: 3
atgttgaagt tcaaatatgg agcgcggaat cctttggatg ctggtgctgc tgaacccatt      60
gccagccggg cctccaggct gaatctgttc ttccagggga aaccacccct tatgactcaa     120
cagcagatgt ctcctctttc ccgagaaggg atattagatg ccctctttgt tctctttgaa     180
gaatgcagtc agcctgctct gatgaagatt aagcacgtga gcaactttgt ccggaagtat     240
tccgacacca tagctgagtt acaggagctc cagccttcgg caaaggactt cgaagtcaga     300
agtcttgtag gttgtggtca ctttgctgaa gtgcaggtgg taagagagaa agcaaccggg     360
gacatctatg ctatgaaagt gatgaagaag aaggctttat tggcccagga gcaggtttca     420
ttttttgagg aagagcggaa catattatct cgaagcacaa gcccgtggat ccccaatta     480
cagtatgcct ttcaggacaa aaatcacctt tatctggtca tggaatatca gcctggaggg     540
gacttgctgt cacttttgaa tagatatgag gaccagttag atgaaaacct gatacagttt     600
tacctagctg agctgatttt ggctgttcac agcgttcatc tgatgggata cgtgcatcga     660
gacatcaagc tgagaacat tctcgttgac cgcacaggac acatcaagct ggtggatttt     720
ggatctgccg cgaaaatgaa ttcaaacaag atggtgaatg ccaaactccc gattgggacc     780
ccagattaca tggctcctga agtgctgact gtgatgaacg gggatggaaa aggcacctac     840
ggcctggact gtgactggtg gtcagtgggc gtgattgcct atgagatgat ttatgggaga     900
tccccctttcg cagagggaac ctctgccaga accttcaata acattatgaa tttccagcgg     960
tttttgaaat tccagatgaa ccccaaagtg agcagtgact tcttgatct gattcaaagc    1020
ttgttgtgcg gccagaaaga gagactgaag tttgaaggtc tttgctgcca tcctttcttc    1080
tctaaaattg actggaacaa cattcgtaac tctcctcccc ccttcgttcc caccctcaag    1140
tctgacgatg acacctccaa ttttgatgaa ccagagaaga attcgtgggt ttcatcctct    1200
ccgtgccagc tgagcccctc aggcttctcg ggtgaagaac tgccgtttgt gggggttttcg    1260
tacagcaagg cactggggat tcttggtaga tctgagtctg ttgtgtcggg tctggactcc    1320
cctgccaaga ctagctccat ggaaaagaaa cttctcatca aaagcaaaga gctacaagac    1380
tctcaggaca agtgtcacaa gatggagcag gaaatgaccc ggttacatcg gagagtgtca    1440
gaggtggagg ctgtgcttag tcagaaggag gtggagctga aggcctctga gactcagaga    1500
tccctcctgg agcaggacct tgctacctac atcacagaat gcagtagctt aaagcgaagt    1560
ttggagcaag cacggatgga ggtgtcccag gaggatgaca agcactgca gcttctccat    1620
gatatcagag agcagagccg gaagctccaa gaaatcaaag agcaggagta ccaggctcaa    1680
gtggaagaaa tgaggttgat gatgaatcag ttggaagagg atcttgtctc agcaagaaga    1740
cggagtgatc tctacgaatc tgagctgaga gagtctcggc ttgctgctga agaattcaag    1800
cggaaagcga cagaatgtca gcataaactg ttgaaggcta aggatcaagg gaagcctgaa    1860
gtgggagaat atgcgaaact ggagaagatc aatgctgagc agcagctcaa aattcaggag    1920
ctccaagaga aactggagaa ggctgtaaaa gccagcacgg aggccaccga gctgctgcag    1980
aatatccgcc aggcaaagga gcgagccgag agggagctgg agaagctgca gaaccgagag    2040
gattcttctg aaggcatcag aaagaagctg gtggaagctg aggaacgccg ccattctctg    2100
gagaacaagg taagagagact agagaccatg gagcgtagag aaaacagact gaaggatgac    2160
atccagacaa atcccaaca gatccagcag atggctgata aaattctgga gctcgaagag    2220
aaacatcggg aggcccaagt ctcagcccag cacctagaag tgcacctgaa acagaaagag    2280
cagcactatg aggaaaagat taaagtgttg gacaatcaga taaagaaaga cctggctgac    2340
```

-continued

```
aaggagacac tggagaacat gatgcagaga cacgaggagg aggcccatga aagggcaaa    2400
attctcagcg aacagaaggc gatgatcaat gctatggatt ccaagatcag atccctggaa    2460
cagaggattg tggaactgtc tgaagccaat aaacttgcag caaatagcag tcttttttacc   2520
caaaggaaca tgaaggccca agaagagatg atttctgaac tcaggcaaca gaaattttac    2580
ctggagacac aggctgggaa gttggaggcc cagaaccgaa actggagga gcagctggag     2640
aagatcagcc accaagacca cagtgacaag atcggctgc tggaactgga gacaagattg     2700
cgggaggtca gtctagagca cgaggagcag aaactgagc tcaagcgcca gctcacagag     2760
ctacagctct ccctgcagga gcgcgagtca cagttgacag ccctgcaggc tgcacgggcg    2820
gccctggaga gccagcttcg ccaggcgaag acagagctgg aagagaccac agcagaagct    2880
gaagaggaga tccaggcact cacggcacat agagatgaaa tccagcgcaa atttgatgct    2940
cttcgtaaca gctgtactgt aatcacagac ctggaggagc agctaaacca gctgaccgag    3000
gacaacgctg aactcaacaa ccaaaacttc tacttgtcca acaactcga tgaggcttct     3060
ggcgccaacg acgagattgt acaactgcga agtgaagtgg accatctccg ccgggagatc    3120
acggaacgag agatgcagct taccagccag aagcaaacga tggaggctct gaagaccacg    3180
tgcaccatgc tggaggaaca ggtcatggat ttggaggccc taaacgatga gctgctagaa    3240
aaagagcggc agtgggaggc ctggaggagc gtcctgggtg atgagaaatc ccagtttgag    3300
tgtcgggttc gagagctgca gaggatgctg acaccgaga acagagcag ggcgagagcc     3360
gatcagcgga tcaccgagtc tcgccaggtg gtggagctgg cagtgaagga gcacaaggct    3420
gagattctcg ctctgcagca ggctctcaaa gagcagaagc tgaaggccga gagcctctct    3480
gacaagctca atgacctgga gaagaagcat gctatgcttg aaatgaatgc ccgaagctta    3540
cagcagaagc tggagactga acgagagctc aaacagaggc ttctggaaga gcaagccaaa    3600
ttacagcagc agatggacct gcagaaaaat cacattttcc gtctgactca aggactgcaa    3660
gaagctctag atcgggctga tctactgaag acagaaagaa gtgacttgga gtatcagctg    3720
gaaaacattc aggttctcta ttctcatgaa aaggtgaaaa tggaaggcac tatttctcaa    3780
caaaccaaac tcattgattt tctgcaagcc aaaatggacc aacctgctaa aaagaaaaag    3840
gttcctctgc agtacaatga gctgaagctg gccctggaga aggagaaagc tcgctgtgca    3900
gagctagagg aagcccttca gaagacccgc atcgagctcc ggtccgcccg ggaggaagct    3960
gcccaccgca agcaacgga ccacccacac ccatccacgc cagccaccgc gaggcagcag    4020
atcgccatgt ccgccatcgt gcggtcgcca gagcaccagc ccagtgccat gagcctgctg    4080
gccccgccat ccagccgcag aaaggagtct tcaactccag aggaatttag tcggcgtctt    4140
aaggaacgca tgcaccacaa tattcctcac cgattcaacg taggactgaa catgcgagcc    4200
acaaagtgtg ctgtgtgtct ggataccgtg cactttggac gccaggcatc caaatgtctc    4260
gaatgtcagg tgatgtgtca ccccaagtgc tccacgtgct tgccagccac ctgcggcttg    4320
cctgctgaat atgccacaca cttcaccgag gccttctgcc gtgacaaaat gaactcccca    4380
ggtctccaga ccaaggagcc cagcagcagc ttgcacctgg aagggtggat gaaggtgccc    4440
aggaataaca aacgaggaca gcaaggctgg acaggaagt acattgtcct ggagggatca    4500
aaagtcctca tttatgacaa tgaagccaga gaagctggac agaggccggt ggaagaattt    4560
gagctgtgcc ttcccgacgg ggatgtatct attcatggtg ccgttggtgc ttccgaactc    4620
gcaaatacag ccaaagcaga tgtcccatac atactgaaga tggaatctca cccgcacacc    4680
```

-continued

```
acctgctggc ccgggagaac cctctacttg ctagctccca gcttccctga caaacagcgc    4740
tgggtcaccg ccttagaatc agttgtcgca ggtgggagag tttctaggga aaaagcagaa    4800
gctgatgcta aactgcttgg aaactccctg ctgaaactgg aaggtgatga ccgtctagac    4860
atgaactgca cgctgccctt cagtgaccag gtggtgttgg tgggcaccga ggaagggctc    4920
tacgccctga atgtcttgaa aaactcccta acccatgtcc caggaattgg agcagtcttc    4980
caaatttata ttatcaagga cctggagaag ctactcatga tagcaggaga agagcgggca    5040
ctgtgtcttg tggacgtgaa gaaagtgaaa cagtccctgg cccagtccca cctgcctgcc    5100
cagcccgaca tctcacccaa cattttgaa gctgtcaagg gctgccactt gtttggggca    5160
ggcaagattg agaacgggct ctgcatctgt gcagccatgc ccagcaaagt cgtcattctc    5220
cgctacaacg aaaacctcag caaatactgc atccggaaag agatagagac ctcagagccc    5280
tgcagctgta tccacttcac caattacagt atcctcattg gaaccaataa attctacgaa    5340
atcgacatga agcagtacac gctcgaggaa ttcctggata agaatgacca ttccttggca    5400
cctgctgtgt tgccgcctc ttccaacagc ttccctgtct caatcgtgca ggtgaacagc    5460
gcagggcagc gagaggagta cttgctgtgt ttccacgaat ttggagtgtt cgtggattct    5520
tacggaagac gtagccgcac agacgatctc aagtggagtc gcttaccttt ggcctttgcc    5580
tacagagaac cctatctgtt tgtgacccac ttcaactcac tcgaagtaat tgagatccag    5640
gcacgctcct cagcagggac ccctgcccga gcgtacctgg acatcccgaa cccgcgctac    5700
ctgggccctg ccatttcctc aggagcgatt tacttggcgt cctcatacca ggataaatta    5760
agggtcattt gctgcaaggg aaacctcgtg aaggagtccg gcactgaaca ccaccggggc    5820
ccgtccacct cccgcagatt tcaaagccat atggctagag atgaatataa accttga     5877
```

<210> SEQ ID NO 4
<211> LENGTH: 1958
<212> TYPE: PRT
<213> ORGANISM: homo sapiens

<400> SEQUENCE: 4

```
Met Leu Lys Phe Lys Tyr Gly Ala Arg Asn Pro Leu Asp Ala Gly Ala
  1               5                  10                  15

Ala Glu Pro Ile Ala Ser Arg Ala Ser Arg Leu Asn Leu Phe Phe Gln
             20                  25                  30

Gly Lys Pro Pro Phe Met Thr Gln Gln Gln Met Ser Pro Leu Ser Arg
         35                  40                  45

Glu Gly Ile Leu Asp Ala Leu Phe Val Leu Phe Glu Glu Cys Ser Gln
     50                  55                  60

Pro Ala Leu Met Lys Ile Lys His Val Ser Asn Phe Val Arg Lys Tyr
 65                  70                  75                  80

Ser Asp Thr Ile Ala Glu Leu Gln Glu Leu Gln Pro Ser Ala Lys Asp
                 85                  90                  95

Phe Glu Val Arg Ser Leu Val Gly Cys Gly His Phe Ala Glu Val Gln
            100                 105                 110

Val Val Arg Glu Lys Ala Thr Gly Asp Ile Tyr Ala Met Lys Val Met
        115                 120                 125

Lys Lys Lys Ala Leu Leu Ala Gln Glu Gln Val Ser Phe Phe Glu Glu
    130                 135                 140

Glu Arg Asn Ile Leu Ser Arg Ser Thr Ser Pro Trp Ile Pro Gln Leu
145                 150                 155                 160

Gln Tyr Ala Phe Gln Asp Lys Asn His Leu Tyr Leu Val Met Glu Tyr
```

-continued

```
                165                 170                 175
Gln Pro Gly Gly Asp Leu Leu Ser Leu Leu Asn Arg Tyr Glu Asp Gln
                    180                 185                 190
Leu Asp Glu Asn Leu Ile Gln Phe Tyr Leu Ala Glu Leu Ile Leu Ala
                195                 200                 205
Val His Ser Val His Leu Met Gly Tyr Val His Arg Asp Ile Lys Pro
            210                 215                 220
Glu Asn Ile Leu Val Asp Arg Thr Gly His Ile Lys Leu Val Asp Phe
225                 230                 235                 240
Gly Ser Ala Ala Lys Met Asn Ser Asn Lys Met Val Asn Ala Lys Leu
                        245                 250                 255
Pro Ile Gly Thr Pro Asp Tyr Met Ala Pro Glu Val Leu Thr Val Met
                260                 265                 270
Asn Gly Asp Gly Lys Gly Thr Tyr Gly Leu Asp Cys Asp Trp Trp Ser
                275                 280                 285
Val Gly Val Ile Ala Tyr Glu Met Ile Tyr Gly Arg Ser Pro Phe Ala
            290                 295                 300
Glu Gly Thr Ser Ala Arg Thr Phe Asn Asn Ile Met Asn Phe Gln Arg
305                 310                 315                 320
Phe Leu Lys Phe Pro Asp Asp Pro Lys Val Ser Ser Asp Phe Leu Asp
                    325                 330                 335
Leu Ile Gln Ser Leu Leu Cys Gly Gln Lys Glu Arg Leu Lys Phe Glu
                340                 345                 350
Gly Leu Cys Cys His Pro Phe Phe Ser Lys Ile Asp Trp Asn Asn Ile
                355                 360                 365
Arg Asn Ser Pro Pro Phe Val Pro Thr Leu Lys Ser Asp Asp Asp
370                 375                 380
Thr Ser Asn Phe Asp Glu Pro Glu Lys Asn Ser Trp Val Ser Ser Ser
385                 390                 395                 400
Pro Cys Gln Leu Ser Pro Ser Gly Phe Ser Gly Glu Glu Leu Pro Phe
                    405                 410                 415
Val Gly Phe Ser Tyr Ser Lys Ala Leu Gly Ile Leu Gly Arg Ser Glu
                420                 425                 430
Ser Val Val Ser Gly Leu Asp Ser Pro Ala Lys Thr Ser Ser Met Glu
            435                 440                 445
Lys Lys Leu Leu Ile Lys Ser Lys Glu Leu Gln Asp Ser Gln Asp Lys
        450                 455                 460
Cys His Lys Met Glu Gln Glu Met Thr Arg Leu His Arg Arg Val Ser
465                 470                 475                 480
Glu Val Glu Ala Val Leu Ser Gln Lys Glu Val Glu Leu Lys Ala Ser
                    485                 490                 495
Glu Thr Gln Arg Ser Leu Leu Glu Gln Asp Leu Ala Thr Tyr Ile Thr
                500                 505                 510
Glu Cys Ser Ser Leu Lys Arg Ser Leu Glu Gln Ala Arg Met Glu Val
            515                 520                 525
Ser Gln Glu Asp Asp Lys Ala Leu Gln Leu Leu His Asp Ile Arg Glu
        530                 535                 540
Gln Ser Arg Lys Leu Gln Glu Ile Lys Glu Gln Glu Tyr Gln Ala Gln
545                 550                 555                 560
Val Glu Glu Met Arg Leu Met Met Asn Gln Leu Glu Glu Asp Leu Val
                    565                 570                 575
Ser Ala Arg Arg Arg Ser Asp Leu Tyr Glu Ser Glu Leu Arg Glu Ser
                580                 585                 590
```

```
Arg Leu Ala Ala Glu Glu Phe Lys Arg Lys Ala Thr Glu Cys Gln His
            595                 600                 605

Lys Leu Leu Lys Ala Lys Asp Gln Gly Lys Pro Glu Val Gly Glu Tyr
        610                 615                 620

Ala Lys Leu Glu Lys Ile Asn Ala Glu Gln Gln Leu Lys Ile Gln Glu
625                 630                 635                 640

Leu Gln Glu Lys Leu Glu Lys Ala Val Lys Ala Ser Thr Glu Ala Thr
                645                 650                 655

Glu Leu Leu Gln Asn Ile Arg Gln Ala Lys Glu Arg Ala Glu Arg Glu
            660                 665                 670

Leu Glu Lys Leu Gln Asn Arg Glu Asp Ser Ser Glu Gly Ile Arg Lys
        675                 680                 685

Lys Leu Val Glu Ala Glu Arg Arg His Ser Leu Glu Asn Lys Val
690                 695                 700

Lys Arg Leu Glu Thr Met Glu Arg Arg Glu Asn Arg Leu Lys Asp Asp
705                 710                 715                 720

Ile Gln Thr Lys Ser Gln Gln Ile Gln Gln Met Ala Asp Lys Ile Leu
                725                 730                 735

Glu Leu Glu Glu Lys His Arg Glu Ala Gln Val Ser Ala Gln His Leu
            740                 745                 750

Glu Val His Leu Lys Gln Lys Glu Gln His Tyr Glu Glu Lys Ile Lys
        755                 760                 765

Val Leu Asp Asn Gln Ile Lys Lys Asp Leu Ala Asp Lys Glu Thr Leu
        770                 775                 780

Glu Asn Met Met Gln Arg His Glu Glu Glu Ala His Glu Lys Gly Lys
785                 790                 795                 800

Ile Leu Ser Glu Gln Lys Ala Met Ile Asn Ala Met Asp Ser Lys Ile
                805                 810                 815

Arg Ser Leu Glu Gln Arg Ile Val Glu Leu Ser Glu Ala Asn Lys Leu
            820                 825                 830

Ala Ala Asn Ser Ser Leu Phe Thr Gln Arg Asn Met Lys Ala Gln Glu
        835                 840                 845

Glu Met Ile Ser Glu Leu Arg Gln Gln Lys Phe Tyr Leu Glu Thr Gln
850                 855                 860

Ala Gly Lys Leu Glu Ala Gln Asn Arg Lys Leu Glu Glu Gln Leu Glu
865                 870                 875                 880

Lys Ile Ser His Gln Asp His Ser Asp Lys Asn Arg Leu Leu Glu Leu
                885                 890                 895

Glu Thr Arg Leu Arg Glu Val Ser Leu Glu His Glu Glu Gln Lys Leu
            900                 905                 910

Glu Leu Lys Arg Gln Leu Thr Glu Leu Gln Leu Ser Leu Gln Glu Arg
        915                 920                 925

Glu Ser Gln Leu Thr Ala Leu Gln Ala Ala Arg Ala Ala Leu Glu Ser
        930                 935                 940

Gln Leu Arg Gln Ala Lys Thr Glu Leu Glu Glu Thr Thr Ala Glu Ala
945                 950                 955                 960

Glu Glu Glu Ile Gln Ala Leu Thr Ala His Arg Asp Glu Ile Gln Arg
                965                 970                 975

Lys Phe Asp Ala Leu Arg Asn Ser Cys Thr Val Ile Thr Asp Leu Glu
            980                 985                 990

Glu Gln Leu Asn Gln Leu Thr Glu Asp Asn Ala Glu Leu Asn Asn Gln
        995                 1000                1005
```

-continued

```
Asn Phe Tyr Leu Ser Lys Gln Leu Asp Glu Ala Ser Gly Ala Asn Asp
        1010                1015                1020
Glu Ile Val Gln Leu Arg Ser Glu Val Asp His Leu Arg Arg Glu Ile
1025                1030                1035                1040
Thr Glu Arg Glu Met Gln Leu Thr Ser Gln Lys Gln Thr Met Glu Ala
            1045                1050                1055
Leu Lys Thr Thr Cys Thr Met Leu Glu Glu Gln Val Met Asp Leu Glu
            1060                1065                1070
Ala Leu Asn Asp Glu Leu Leu Glu Lys Glu Arg Gln Trp Glu Ala Trp
            1075                1080                1085
Arg Ser Val Leu Gly Asp Glu Lys Ser Gln Phe Glu Cys Arg Val Arg
            1090                1095                1100
Glu Leu Gln Arg Met Leu Asp Thr Glu Lys Gln Ser Arg Ala Arg Ala
1105                1110                1115                1120
Asp Gln Arg Ile Thr Glu Ser Arg Gln Val Val Glu Leu Ala Val Lys
                1125                1130                1135
Glu His Lys Ala Glu Ile Leu Ala Leu Gln Gln Ala Leu Lys Glu Gln
            1140                1145                1150
Lys Leu Lys Ala Glu Ser Leu Ser Asp Lys Leu Asn Asp Leu Glu Lys
            1155                1160                1165
Lys His Ala Met Leu Glu Met Asn Ala Arg Ser Leu Gln Gln Lys Leu
            1170                1175                1180
Glu Thr Glu Arg Glu Leu Lys Gln Arg Leu Leu Glu Glu Gln Ala Lys
1185                1190                1195                1200
Leu Gln Gln Gln Met Asp Leu Gln Lys Asn His Ile Phe Arg Leu Thr
                1205                1210                1215
Gln Gly Leu Gln Glu Ala Leu Asp Arg Ala Asp Leu Leu Lys Thr Glu
                1220                1225                1230
Arg Ser Asp Leu Glu Tyr Gln Leu Glu Asn Ile Gln Val Leu Tyr Ser
            1235                1240                1245
His Glu Lys Val Lys Met Glu Gly Thr Ile Ser Gln Gln Thr Lys Leu
            1250                1255                1260
Ile Asp Phe Leu Gln Ala Lys Met Asp Gln Pro Ala Lys Lys Lys Lys
1265                1270                1275                1280
Val Pro Leu Gln Tyr Asn Glu Leu Lys Leu Ala Leu Glu Lys Glu Lys
                1285                1290                1295
Ala Arg Cys Ala Glu Leu Glu Glu Ala Leu Gln Lys Thr Arg Ile Glu
            1300                1305                1310
Leu Arg Ser Ala Arg Glu Glu Ala Ala His Arg Lys Ala Thr Asp His
            1315                1320                1325
Pro His Pro Ser Thr Pro Ala Thr Ala Arg Gln Gln Ile Ala Met Ser
        1330                1335                1340
Ala Ile Val Arg Ser Pro Glu His Gln Pro Ser Ala Met Ser Leu Leu
1345                1350                1355                1360
Ala Pro Pro Ser Ser Arg Arg Lys Glu Ser Ser Thr Pro Glu Glu Phe
                1365                1370                1375
Ser Arg Arg Leu Lys Glu Arg Met His His Asn Ile Pro His Arg Phe
            1380                1385                1390
Asn Val Gly Leu Asn Met Arg Ala Thr Lys Cys Ala Val Cys Leu Asp
            1395                1400                1405
Thr Val His Phe Gly Arg Gln Ala Ser Lys Cys Leu Glu Cys Gln Val
        1410                1415                1420
Met Cys His Pro Lys Cys Ser Thr Cys Leu Pro Ala Thr Cys Gly Leu
```

-continued

```
         1425                1430                1435                1440
Pro Ala Glu Tyr Ala Thr His Phe Thr Glu Ala Phe Cys Arg Asp Lys
                 1445                1450                1455
Met Asn Ser Pro Gly Leu Gln Thr Lys Glu Pro Ser Ser Ser Leu His
             1460                1465                1470
Leu Glu Gly Trp Met Lys Val Pro Arg Asn Asn Lys Arg Gly Gln Gln
         1475                1480                1485
Gly Trp Asp Arg Lys Tyr Ile Val Leu Glu Gly Ser Lys Val Leu Ile
     1490                1495                1500
Tyr Asp Asn Glu Ala Arg Glu Ala Gly Gln Arg Pro Val Glu Glu Phe
1505                1510                1515                1520
Glu Leu Cys Leu Pro Asp Gly Asp Val Ser Ile His Gly Ala Val Gly
                 1525                1530                1535
Ala Ser Glu Leu Ala Asn Thr Ala Lys Ala Asp Val Pro Tyr Ile Leu
             1540                1545                1550
Lys Met Glu Ser His Pro His Thr Thr Cys Trp Pro Gly Arg Thr Leu
         1555                1560                1565
Tyr Leu Leu Ala Pro Ser Phe Pro Asp Lys Gln Arg Trp Val Thr Ala
     1570                1575                1580
Leu Glu Ser Val Val Ala Gly Gly Arg Val Ser Arg Glu Lys Ala Glu
1585                1590                1595                1600
Ala Asp Ala Lys Leu Leu Gly Asn Ser Leu Leu Lys Leu Glu Gly Asp
                 1605                1610                1615
Asp Arg Leu Asp Met Asn Cys Thr Leu Pro Phe Ser Asp Gln Val Val
             1620                1625                1630
Leu Val Gly Thr Glu Glu Gly Leu Tyr Ala Leu Asn Val Leu Lys Asn
         1635                1640                1645
Ser Leu Thr His Val Pro Gly Ile Gly Ala Val Phe Gln Ile Tyr Ile
     1650                1655                1660
Ile Lys Asp Leu Glu Lys Leu Leu Met Ile Ala Gly Glu Glu Arg Ala
1665                1670                1675                1680
Leu Cys Leu Val Asp Val Lys Lys Val Lys Gln Ser Leu Ala Gln Ser
                 1685                1690                1695
His Leu Pro Ala Gln Pro Asp Ile Ser Pro Asn Ile Phe Glu Ala Val
             1700                1705                1710
Lys Gly Cys His Leu Phe Gly Ala Gly Lys Ile Glu Asn Gly Leu Cys
         1715                1720                1725
Ile Cys Ala Ala Met Pro Ser Lys Val Val Ile Leu Arg Tyr Asn Glu
     1730                1735                1740
Asn Leu Ser Lys Tyr Cys Ile Arg Lys Glu Ile Glu Thr Ser Glu Pro
1745                1750                1755                1760
Cys Ser Cys Ile His Phe Thr Asn Tyr Ser Ile Leu Ile Gly Thr Asn
                 1765                1770                1775
Lys Phe Tyr Glu Ile Asp Met Lys Gln Tyr Thr Leu Glu Glu Phe Leu
             1780                1785                1790
Asp Lys Asn Asp His Ser Leu Ala Pro Ala Val Phe Ala Ala Ser Ser
         1795                1800                1805
Asn Ser Phe Pro Val Ser Ile Val Gln Val Asn Ser Ala Gly Gln Arg
     1810                1815                1820
Glu Glu Tyr Leu Leu Cys Phe His Glu Phe Gly Val Phe Val Asp Ser
1825                1830                1835                1840
Tyr Gly Arg Arg Ser Arg Thr Asp Asp Leu Lys Trp Ser Arg Leu Pro
                 1845                1850                1855
```

-continued

```
Leu Ala Phe Ala Tyr Arg Glu Pro Tyr Leu Phe Val Thr His Phe Asn
            1860                1865                1870

Ser Leu Glu Val Ile Glu Ile Gln Ala Arg Ser Ser Ala Gly Thr Pro
        1875                1880                1885

Ala Arg Ala Tyr Leu Asp Ile Pro Asn Pro Arg Tyr Leu Gly Pro Ala
    1890                1895                1900

Ile Ser Ser Gly Ala Ile Tyr Leu Ala Ser Ser Tyr Gln Asp Lys Leu
1905                1910                1915                1920

Arg Val Ile Cys Cys Lys Gly Asn Leu Val Lys Glu Ser Gly Thr Glu
                1925                1930                1935

His His Arg Gly Pro Ser Thr Ser Arg Arg Phe Gln Ser His Met Ala
            1940                1945                1950

Arg Asp Glu Tyr Lys Pro
        1955
```

HUMAN KINASES AND POLYNUCLEOTIDES ENCODING THE SAME

The present application claims the benefit of U.S. Provisional Application No. 60/258,335 which was filed on Dec. 27, 2000 and is herein incorporated by reference in its entirety.

1. INTRODUCTION

The present invention relates to the discovery, identification, and characterization of novel human polynucleotides encoding proteins sharing sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over-express the disclosed genes, antagonists and agonists of the proteins, and other compounds that modulate the expression or activity of the proteins encoded by the disclosed genes, which can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins and the corresponding amino acid sequences of these proteins. The novel human proteins (NHPs) described for the first time herein share structural similarity with animal kinases, including, but not limited to, serine-threonine kinases, and particularly Citron rho-interacting kinases. The described sequences describe a full length version of previously reported proteins that were erroneously presumed to be full length. Accordingly, the described NHPs encode novel kinases having homologues and orthologs across a range of phyla and species.

The novel human polynucleotides described herein, encode alternative open reading frames (ORFs) encoding proteins of 2054 and 1958 amino acids in length (see respectively SEQ ID NOS: 2 and 4).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-out" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–4 are "knocked-out") they provide a method of identifying phenotypic expression of the particular gene as well as a method of assigning function to previously unknown genes. In addition, animals in which the unique NHP sequences described in SEQ ID NOS:1–4 are "knocked-out" provide a unique source in which to elicit antibodies to homologous and orthologous proteins which would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–4 are useful for the identification of protein coding sequence and mapping a unique gene to a particular chromosome. These sequences identify actual, biologically verified, and therefore relevant, exon splice junctions as opposed to those that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins.

5. DETAILED DESCRIPTION OF THE INVENTION

The NHPs described for the first time herein are novel proteins whose expression can be detected in, inter alia, human cell lines and human testis, small intestine, fetal kidney, 6- and 9-week embryos, adenocarcinoma, osteosarcoma, and embryonic carcinoma cells. The described sequences were compiled from sequences available in GENBANK (AC016922), and cDNAs generated from human fetal kidney, testis, and lymph node mRNAs (Edge Biosystems, Gaithersburg, Md.) that were identified using primers generated from human genomic DNA.

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of an NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor/ligand binding domain, accessory protein/ self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & Sons, Inc., NY, at p. 2.10.3) and encodes a functionally equivalent expression product. Additionally, contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. Nos. 5,837,458 or 5,723,323 both of which are herein incorporated by reference). The invention also includes degenerate nucleic acid variants of the disclosed NHP polynucleotide sequences.

Additionally contemplated are polynucleotides encoding NHP ORFS, or their functional equivalents, encoded by polynucleotide sequences that are about 99, 95, 90, or about 85 percent similar to corresponding regions of SEQ ID NO:1 (as measured by BLAST sequence comparison analysis using, for example, the GCG sequence analysis package using default parameters).

The invention also includes nucleic acid molecules, preferably DNA molecules, that hybridize to, and are therefore the complements of, the described NHP encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–4 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–4, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–4 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–4.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–4 provides detailed information about transcriptional changes involved in a specific pathway, potentially leading to the identification of novel components or gene functions that manifest themselves as novel phenotypes.

Probes consisting of sequences first disclosed in SEQ ID NOS:1–4 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–4 can be utilized in microarrays or other assay formats, to screen collections of genetic material from patients who have a particular medical condition. These investigations can also be carried out using the sequences first disclosed in SEQ ID NOS:1–4 in silico and by comparing previously collected genetic databases and the disclosed sequences using computer software known to those in the art.

Thus the sequences first disclosed in SEQ ID NOS:1–4 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–4. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation and/or as antisense primers in amplification reactions of NHP gene nucleic acid sequences. With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, NY; and Ausubel et al., 1989, Current Protocols in Molecular Biology, Green Publishing Associates and Wiley Interscience, NY.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from, for example, human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, behavioral disorders, immune disorders, obesity, high blood pressure, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue may be expressed and screened using standard antibody screening techniques in conjunction with antibodies raised against a normal NHP product, as described below. For screening techniques, see, for example, Harlow, E. and Lane, eds., 1988, "Antibodies: A Laboratory Manual", Cold Spring Harbor Press, Cold Spring Harbor, N.Y.

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well-known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323 which are herein incorporated by reference in their entirety.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHP peptides or polypeptides are thought to be cytoplasmic or nuclear proteins (although processed forms or fragments can be secreted or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing.

Expression analysis has provided evidence that the described NHPs can be expressed in a relatively narrow range of human tissues. In addition to serine-threonine kinases, the described NHPs also share significant similarity to a range of additional kinase families, including Citron kinases from a variety of phyla and species (for example GENBANK AF086824 and U39904). Several polymorphisms were detected in the described NHPs including a C/G polymorphism at the region represented by nucleotide position number 5218 of, for example, SEQ ID NO:1 which can result in a leu or val being present at corresponding amino acid (aa) position 1740 of, for example, SEQ ID NO:2, and a C/G polymorphism at the region represented by nucleotide position number 6065 of, for example, SEQ ID NO:1 which can result in an ala or gly being present at corresponding amino acid position 2022 of, for example, SEQ ID NO:2.

The gene encoding the described NHPs is apparently encoded on human chromosome 12.

The described novel human polynucleotide sequences can be used, among other things, in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus-mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell-type, thus inactivating the endogenous NHP gene in only that cell-type, by following, for example, the teaching of Gu et al., 1994, Science, 265:103–106. The regulatory sequences required for such a cell-type specific inactivation will depend upon the particular cell-type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHP gene-expressing tissue, may also be evaluated immunocytochemically using antibodies specific for the NHP transgene product.

The present invention provides for "knockin" animals. Knockin animals are those in which a gene that the animal does not naturally have in its genome, is inserted. For example, when a human gene is used to replace its murine ortholog in the mouse. Such knockin animals are useful for the in vivo study, testing and validation of, intra alia, human drug targets as well as for compounds that are directed at the same.

5.2 NHPs and NHP Polypeptides

NHP products, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to the NHP, as reagents in assays for screening for compounds that can be used as pharmaceutical reagents useful in the therapeutic treatment of mental, biological, or medical disorders and disease (including cancer).

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display consensus signal sequences which indicates that they may be cytoplasmic or possibly nuclear proteins, although they may also be secreted or membrane associated.

The NHP amino acid sequences of the invention include the amino acid sequences presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing, is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and modify a NHP substrate, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of the NHP, but to assess biological activity, e.g., in certain drug screening assays.

The expression systems that may be used for purposes of the invention include, but are not limited to, microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk⁻, hgprt⁻ or aprt⁻ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$·nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes:A Practical Approach", New, R.R.C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. Nos. 60/111, 701 and 60/056,713, both of which are herein incorporated by reference, for examples of such transducing sequences) to facilitate passage across cellular membranes and can optionally be engineered to include nuclear localization.

5.3 Antibodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention can be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with the NHP, a NHP peptide (e.g., one corresponding to a functional domain of a NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA, 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies or Fab fragments of such anti-idiotypes can be used in therapeutic regimens involving a NHP-mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence described in SEQ ID NO: 1.

2. An isolated nucleic acid molecule comprising a nucleotide sequence that:
   (a) encodes the amino acid sequence shown in SEQ ID NO: 2; and
   (b) hybridizes under stringent conditions to the nucleotide sequence of SEQ ID NO: 1 or the complement thereof.

3. An isolated nucleic acid molecule comprising a nucleotide sequence that encodes the amino acid sequence shown in SEQ ID NO: 2.

4. A recombinant expression vector comprising a nucleic acid molecule of claim 3.

5. A host cell comprising the expression vector of claim 4.

* * * * *